United States Patent
Chi

(10) Patent No.: US 8,192,835 B2
(45) Date of Patent: Jun. 5, 2012

(54) BONE SUBSTITUTE MATERIAL

(75) Inventor: Charles Chi, San Francisco, CA (US)

(73) Assignee: Charlie W. Chi, San Francisco, CA (US)

(*) Notice: Subject to any disclaimer, the term of this patent is extended or adjusted under 35 U.S.C. 154(b) by 0 days.

(21) Appl. No.: 12/708,438

(22) Filed: Feb. 18, 2010

(65) Prior Publication Data

US 2010/0211183 A1 Aug. 19, 2010

Related U.S. Application Data

(63) Continuation of application No. 11/212,977, filed on Aug. 26, 2005, now Pat. No. 7,687,098.

(51) Int. Cl.
*B32B 5/16* (2006.01)
*A61F 2/28* (2006.01)

(52) U.S. Cl. ........... 428/323; 428/327; 623/16.11; 623/23.51; 623/23.61

(58) Field of Classification Search ............... None
See application file for complete search history.

(56) References Cited

U.S. PATENT DOCUMENTS

| | | |
|---|---|---|
| 4,349,518 A | 9/1982 | Long et al. |
| 4,407,262 A | 10/1983 | Wirz et al. |
| 4,702,930 A | 10/1987 | Heide et al. |
| 5,188,670 A | 2/1993 | Constantz |
| 5,486,365 A | 1/1996 | Takado et al. |
| 5,593,741 A | 1/1997 | Ikeda |
| 5,728,425 A | 3/1998 | Ebe et al. |
| 5,730,801 A | 3/1998 | Tepman et al. |
| 6,129,928 A | 10/2000 | Sarangapani et al. |
| 6,183,564 B1 | 2/2001 | Reynolds et al. |
| 6,296,667 B1 * | 10/2001 | Johnson et al. ......... 623/23.61 |
| 6,384,196 B1 * | 5/2002 | Weis et al. ............... 530/356 |
| 6,409,837 B1 | 6/2002 | Hillman |
| 6,455,098 B2 | 9/2002 | Tran et al. |
| 6,613,105 B1 | 9/2003 | Moore |
| 6,840,961 B2 * | 1/2005 | Tofighi et al. ......... 623/23.61 |
| 6,846,853 B2 | 1/2005 | Shimp |
| 7,390,335 B2 | 6/2008 | Chow |
| 7,687,098 B1 | 3/2010 | Chi |
| 2005/0226939 A1 | 10/2005 | Ramalingam et al. |
| 2007/0059379 A1 | 3/2007 | Gerber |
| 2010/0206228 A1 | 8/2010 | Chi |

OTHER PUBLICATIONS

Tadic et al., "Continuous synthesis of amorphous carbonated apatites," Biomaterials, vol. 23, pp. 2553-2559, 2002.

* cited by examiner

*Primary Examiner* — Sheeba Ahmed
(74) *Attorney, Agent, or Firm* — Dorsey & Whitney LLP

(57) ABSTRACT

A method for fabricating a substitute component for bone, including the processes of: provision of a chemical spray including at least three of calcium chloride, hydrogen phosphate, hydrogen carbonate and water to form a combined solution; reaction and precipitation of the combined solution onto a substrate; allowing the precipitated particles to form a porous structure on the substrate; applying substantially isostatic pressure to the porous structure to form a compressed structure; and (optional) providing one or more through-holes in the compressed structure to promote osteoinduction.

11 Claims, 15 Drawing Sheets

BONE SUBSTITUTE MATERIAL

CROSS REFERENCE TO RELATED APPLICATIONS

This application is a continuation application of and claims priority under 35 U.S.C. §120 to U.S. patent application Ser. No. 11/212,977, now U.S. Pat. No. 7,687,098, entitled Chemical Mechanical Vapor Deposition Device for Production of Bone Substitute Material, filed Aug. 26, 2005, and which is hereby incorporated by reference in its entirety as though fully set forth herein.

This application is also related to co-pending U.S. patent application Ser. No. 12/708,425, entitled Chemical Mechanical Vapor Deposition Device for Production of Bone Substitute Material, filed on Feb. 18, 2010, and which is hereby incorporated by reference in its entirety as though fully set forth herein.

FIELD OF THE INVENTION

This invention relates to production of calcium phosphate mineral-based bone substitute material using a chemical solution spray deposition device that accommodates porous and composite laminar structures with reinforced biocompatible polymer fibers in order to encourage new bone growth as well as to provide mechanical strength and rigidity comparable to natural bone.

BACKGROUND OF THE INVENTION

Bone is an organ composed of hard living tissue providing structural support to the body—it serves as scaffolding. A hard matrix of calcium salts is deposited around protein fibers. Minerals make bone rigid and protein (collagen) provides strength and elasticity. Bone is made of about 70 percent mineral and 30 percent of organic matrix. In an adult, bone engages in a continuous cycle of breaking down and rebuilding. Bone absorbing cells, called osteoclasts, break down bone and discard worn cells. After a few weeks, the osteoclasts disappear, and osteoblasts come to repair the bone. During the cycle, calcium and other minerals are withdrawn from the blood and deposited on the damaged bone surface. The outer layer of bone is called cortical bone; 80 percent of skeletal bone mass is cortical bone. Cancellous bone is an inner spongy structure that resembles honeycomb and accounts for 20 percent of bone mass. The shape of bone is described as long, short, flat, or irregular. The shape is further classified as axial or appendicular. Axial bones are protective. For example, spinal vertebrae protect the spinal cord. Appendicular bones are the limbs. Although there many shapes and sizes of skeletal bone, the bones that make up the spinal column are unique.

Cortical bone is a natural composite which exhibits a rich hierarchical structure. On the microstructural level are the osteons, which are large hollow fibers (about 200 microns in diameter) composed of concentric lamellae and pores. The lamellae are built from fibers, and the fibers contain fibrils. At the ultra-structural level, the fibers are a composite of the mineral hydroxyapatite (HAP) and the protein collagen. These specific structural features are associated with various physical properties. Stiffness of bone arises from the composite structure of mineral crystals and protein fibers. Viscoelastic properties result from slip at bone cement lines between osteon. The cement lines serve as weak interfaces to impart a degree of toughness to bone. As for pores, the lacunae are ellipsoidal pores, which provide space for the osteocytes, the living cells of bone. The pore structure of bone is essential in maintaining its viability and consequently its ability to adapt to mechanical stress. The processes of bone formation (osteogenesis) are involved with osteoinduction and osteoconduction. Osteoconduction is defined as the ability to stimulate the attachment, migration, and distribution of vascular and osteogenic cells within the graft material. Osteoinduction is defined as the ability to stimulate the proliferation and differentiation of pluripotent mesenchymal stem cells. The physical characteristics that affect the graft's osteoconductive activity include porosity, pore size, and three-dimensional architecture. In addition, direct biochemical interactions between matrix protein and cell surface receptors play a major role in the host's response to the graft material. The ability of a graft material to independently produce bone is termed its direct osteogenic potential. To have direct osteogenic activity, the graft preferably contains cellular components that directly induce bone formation.

Natural bone grafts have been extensively used to promote new bone growth (osteogenesis) in the orthopedic industry. Natural bone mineral is fundamentally a mixture of amorphous and crystalline calcium phosphate of HAP (hydroxyapatite) with Ca/P ratio of around 1.6. Natural bone grafts are associated with problems such as limited availability and risky recovery procedure for the autogenous bone, and risks of viral transmission and immune reaction for allograft bone from a cadaver. Consequently, biocompatible matrices are currently being developed to stimulate bone formation via osteoconduction and to promote osteoinduction by using osteogenic growth factors. The biocompatible material should satisfy the following: 1) incorporation and retaining of mesenchymal cells in tissue culture, 2) rapid induction of fibrilvascular invasion from the surrounding tissues, 3) having significant osteoconductive properties with the host bone, 4) no significant immune responses, 5) biomechanical properties similar to normal bone, 6) biodegradable properties with an absorption rate parallel to the rate of new bone deposition, and 7) sites with noncovalently binding osteogenic biomolecules to enhance osteoinduction. Numerous polymeric systems have been studied, including poly-α-hydroxy esters, polydioxanone, propylene fumarate, poly-ethylene glycol, poly-orthoesters, polyanhydrides, etc. These systems have the advantages of being already approved for use in humans and are available with varying porosities in any three-dimensional shape, and have been shown to be an excellent substrate for cellular or bioactive molecule delivery. Other types of materials include HAP (hydroxyapatite) and β-TCP (tricalcium phosphate). They have been the two most intensely studied materials for bone repair and regeneration. Their most unique property is chemical similarity to the mineralization phase of bone. This similarity accounts for their osteoconductive potential and excellent biocompatibility. Both HAP and β-TCP have been shown to be excellent carriers of osteoinduction growth factors and osteogenic cell population. However, by and large, metal, ceramic or polymer materials that have been introduced for bone substitutes have been substantially denser, heavier and significantly stiffer than natural bone although some ceramic materials exhibit similar chemical properties. Natural bone fails gradually when stressed under high compression. By contrast, bone substitute ceramic materials commonly show sudden and catastrophic failure under compression, because most of the bone substitute materials individually lack the several areas of biomechanical properties of natural bone, such as elasticity, viscoelasticity and lamellar structural properties.

What is needed is a calcium phosphate-based bone substitute material, and method of fabrication thereof, that is biocompatible with natural bone, is resorbable for osteogenesis, is rigid, is elastic with reinforced biocompatible polymer fibers, is viscoelasticity through use of multi-layered laminar structures, has controlled porosity, and has pore size(s) comparable to natural bone. The bone substitute should be strong and tough enough to support the spinal column for spinal surgeries as well as many other orthopedic applications.

SUMMARY OF THE INVENTION

These needs are met by the invention, which provides a production device and manufacturing processes, for bone substitute material with excellent osteoconductive and osteoinductive characteristics, that perform chemical solution spray deposition (CSSD) method incorporated with fiber reinforcing, isostatic press. The production device and manufacturing processes presented here rationally simulate natural bone repairing and building processes under various mechanical stresses.

In order to simulate the processes of osteoblasts and osteoclasts in natural bone rebuilding or new bone formation, a chemical solution spray deposition method is presented. In this process, solutions, which include calcium and phosphate ions in separate containers, are mechanically and simultaneously sprayed into an isolated chamber with formation of significant number of small solution particles (500 nanometers to 20 micro meters) in a liquid state. One container contains saturated solution of calcium chloride ($CaCl_2(aq)$). The other container contains saturated solution of hydrogen phosphate ($H_3PO_4(aq)$). Optionally, a third container can be added to contain saturated solution of hydrogen carbonate ($H_2CO_3(aq)$). And finally, another container with distilled water is added into the system to control a degree of saturation during the chemical reaction, i.e., high and low supersaturated states. It is noted that the proportion of phosphate co-precipitated depends on the temperature, pH and the concentration of calcium co-precipitating chemicals.

$$\frac{\text{mass of phosphorus}}{\text{mass of calcium}} = \sigma A h(\text{pH}, Ca, T) \quad (1)$$

where $\sigma$ is the maximum surface density of phosphorus, $A$ is the surface area of phosphorus molecule, and the function $h$ varies between Ca 0.1 and 0.9. This relation predicts the ratio of calcium to phosphorus for chemical formation of calcium phosphates precipitation, leading to the control of pH, the optimal concentration and the desirable particle sizes of each chemical during the chemical solution spray process.

The next step is that the small particles are transported into another isolated chamber by a reciprocating piston motion. By applying appropriate pressure caused by the downward piston motion and temperature to the chamber, the solution particles with calcium ion collide with those with phosphate ion, which induces chemical reaction between calcium and phosphate ions in combination with water molecules to formulate various calcium phosphate precipitates, such as hydroxyapatite (HAP), tricalcium phosphate (TCP), octacalcium phosphate (OCP), and dicalcium phosphate dihydrate (DCDP). One of the equilibrium chemical reactions is expressed as:

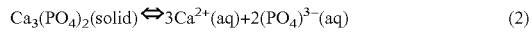
$$Ca_3(PO_4)_2(\text{solid}) \Leftrightarrow 3Ca^{2+}(aq) + 2(PO_4)^{3-}(aq) \quad (2)$$

⇐ equilibrium shift to left in presence of excessive phosphate ion.

The phosphorous contents of the minerals are very similar, and therefore accurate chemical analysis is required to distinguish between these minerals from changes in the solution composition during crystal growth. At high supersaturations, it is difficult to precipitate HAP alone because of the spontaneous formation of precursor phases, such as amorphous DCDP, TCP and OCP. At lower supersaturations, it has been found possible to nucleate HAP in pH conditions where the solutions are slightly under-saturated with respect to amorphous TCP and OCP. The shape growth curve can provide the process information of the percentage crystalline HAP growth on the seeds through progressive amorphous and precursor phases such as TCP, OCP and DCDP. More significantly, the ratio of crystalline to amorphous structures is closely related, not only to mechanical properties, but also to osteoconductive and osteoinductive activities during the fusion process with natural bone. The precipitates of calcium phosphate minerals in both amorphous and crystalline structures move to a final chamber and are finally deposited on the substrate surface, preferably, calcium carbonate. They are accumulated in thickness with the formation of porous structures. The pore size is determined by the solution particle size during the spraying process. More significantly, the production device presented here enables control of various ratios of amorphous to crystalline structures in calcium phosphate minerals by adjusting pressure, temperature, a solution particle size, concentration of chemicals and amount of solvent (distilled water), i.e., pH, based on the shape growth curve.

For the simulation of mechanical properties of protein, which provides elastic property and strength of natural bone, biocompatible polymer fibers, preferably, PEEK (polyetheretherketone), are added to reinforce calcium phosphate minerals during the calcium phosphate mineral deposition. Biocompatible polymers, such as PEEK, have excellent flexural, impact and tensile characteristics. Especially, PEEK is insoluble in all common solvents and, being crystalline, is extremely resistant to attack by a very wide range of organic and inorganic chemicals. It has excellent hydrolysis resistance in boiling water (autoclave sterilization) and good radiation resistance (irradiation sterilization).

When a thin layer of calcium phosphate minerals fully reinforced by polymer fibers is observed, it undergoes an isostatic press process. The isostatic press process is used to simulate the new bone formation under various stresses in a human body. This process provides more compact structures between the calcium phosphate minerals and polymer fibers; furthermore, during the process, the pore size can be controlled in terms of isostatic pressure levels. The process is repeated to deposit additional thin layers until desired overall thickness is obtained inside the production device chamber. Consequently, stiffness of bone substitute arises from the composite structure of calcium phosphate minerals and polymer fibers. Viscoelastic properties can be obtained from slip lines between laminated thin layers of the calcium phosphate minerals.

The slip lines as weak interfaces can represent a degree of toughness and viscoelasticity to bone substitute material. This is an advantage using composite laminar structure. To further increase the compressive strength and rigidity of the bone substitute, thinner calcium carbonate mineral layers, compared to calcium phosphate mineral layers, can be deposited to simulate the natural bone cement slip lines. Also, in order to improve osteoinductive activities, blood vessels which nourish the tissue in natural bone (i.e., Haversian canals and Volkmann's canals) are simulated by introducing a mechanical through-hole device that allows incorporation of a finite number of through holes perpendicular or parallel to laminated directions depending on the application. These features in combination with bone morphogenetic protein (BMP) can significantly increase an osteoinductive activity. Furthermore, extracellular matrix scaffolds (ECM) can be added in combination with the polymer fibers or into transition layers (calcium carbonate layers) between the laminated calcium phosphate mineral layers. Various ECM proteins including collagen, laminin, fibronectin, and glycodaminiglcans, can be added for excellent biological scaffolds. These proteins have the advantages of supporting the migration and differentiation of osteoblastic progenitor cells, facilitate the binding of growth factors responsible for osteogenesis, and resorbing within a reasonably short period of time. At the cellular level, ECM molecules exhibit a variety of activities, including acting as a substrate for cell migration, an adhesive for cell anchorage, a ligand for ions, growth factors, and other bioactive agents. ECM molecules are ideal to form layers or substrates for cell delivery to provide high local concentrations of osteoinductive biomolecules.

The bone substitute material must have a ratio of calcium to phosphate of around 1.6 and at least 70 MPa of compressive strength with slight viscoelastic behavior. In order to further increase compressive strength of bone substitute material, the bulk of bone substitute material can undergo an additional isostatic press process, preferably, with saline solution. The bulk of polymer fiber reinforced calcium phosphate minerals with controlled porosity and composite laminated structures can be fabricated for many different applications in the orthopedic industry. For instance, the bone substitute material can be machined and fabricated for spinal fusion implants, i.e., lumbar and cervical inter-body fusion implants. Consequently, in combination with bone morphogenetic protein (BMP), the bone substitute implants are strong and tough enough to support spinal column with bio-safety and eventually fused with vertebral end bodies.

BRIEF DESCRIPTION OF THE DRAWINGS

The invention is described with reference to the following figures.

DETAILED DESCRIPTION OF THE INVENTION

The invention provides production of a bone substitute material using chemical solution spray deposition (CSSD) and isostatic press processes with reinforced plastic fibers, preferably PEEK, resulting in bone substitute having composite laminated structures with controlled porosity. In order to increase toughness and elastic behavior of bone substitute material comparable to natural bone, the composite laminar structure is introduced with reinforced polymer fibers. In order for bone substitute material to have high compressive strength in load bearing applications, calcium phosphate mineral is deposited and forms a layer with an option of inclusion of calcium carbonate mineral into the calcium phosphate mineral. Another option is that calcium carbonate forms one or more separate thin layers between the calcium phosphate layers. The high compressive strength of calcium carbonate material compared to calcium phosphate can provide additional rigidity of the bone substitute material. In case of any crack formed in a calcium phosphate layer, the calcium carbonate layer combined with polymer fibers can prevent micro cracks from further propagation. On the other hand, the calcium carbonate thin layer can provide the viscoelastic property similar to natural bone cement in bone lamellar structures.

Figure 1:
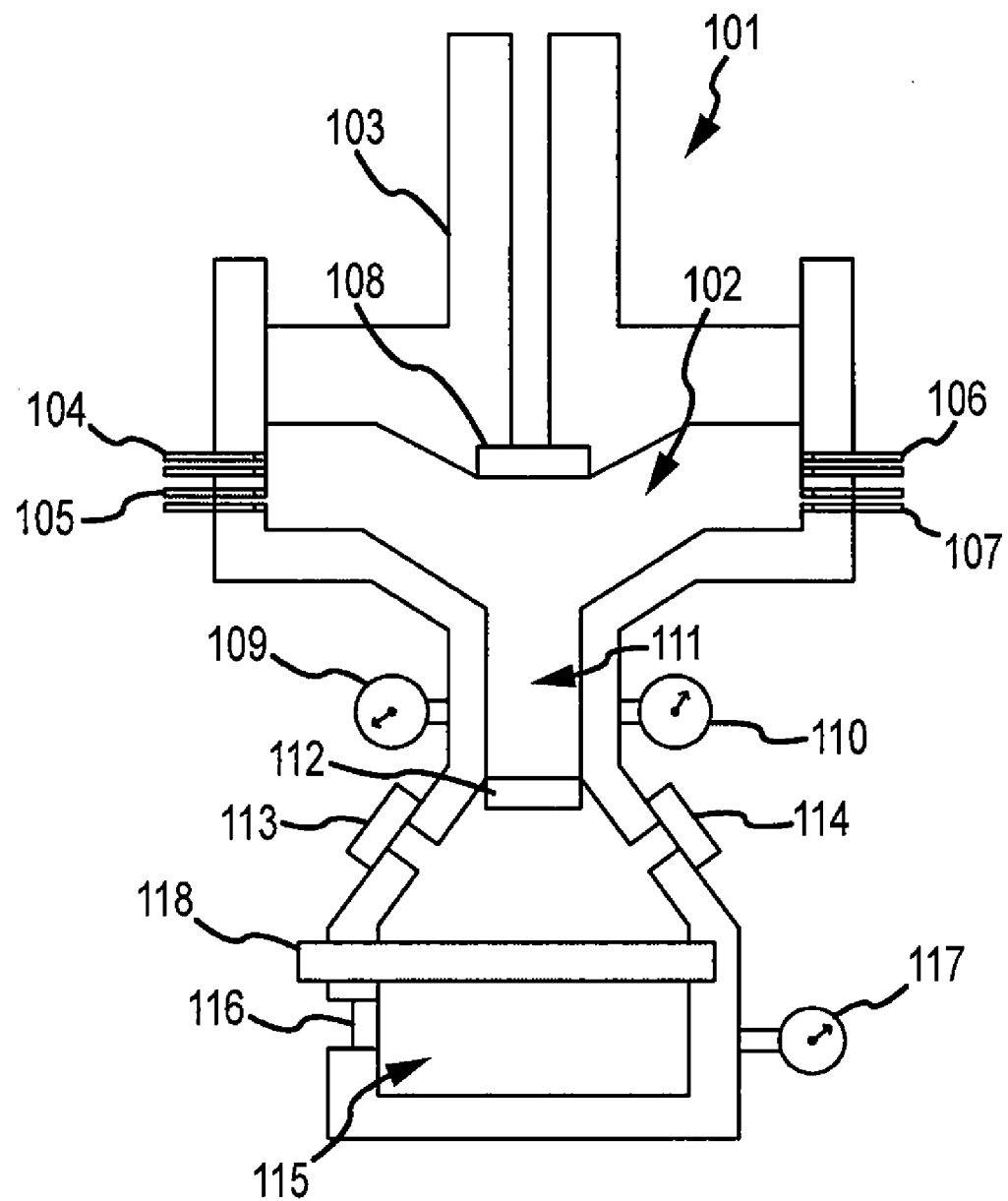
FIG. 1 is a schematic diagram of a bone substitute material production device.

FIG. 1 is a schematic diagram of a bone substitute production device 101. The device 101 consists of three chambers: a primary chamber 102, a secondary chamber 111 and a third chamber 115. In the primary chamber 102, there are four nozzles: 1) calcium chloride solution $CaCl_2(aq)$ spray nozzle 104, 2) distilled water spray nozzle 105, 3) hydrogen phosphate solution $H_3(PO_4)(aq)$ spray nozzle 106 and 4) hydrogen carbonate solution $H_2CO_3(aq)$ spray nozzle 107. The nozzles spray chemical solutions and distilled water with a solution particle size ranging from 500 nanometers to 20 micrometers. Each particle size, concentration and volume inserted into the primary chamber 102 of the solution is different and determined according to Eq. (1) to obtain the optimal amount of the precipitates. The minimum number of nozzles for each solution is at least one and can be higher depending on the size of the device 101. The primary chamber 102 includes a piston 103 with a reciprocating motion and an exhaust valve 108. The downward piston motion 103 pushes the sprayed chemicals into the secondary chamber 111 with an increase of pressure. Depending on the size of the device, multiple numbers of the secondary chambers can be incorporated into the device 101. Also, by the downward motion of the piston 103, the pressure is built up in the secondary chamber 111 and further increases by the closure of a valve 112 and is monitored by a pressure gauge 109. Furthermore, heat, ranging from room temperature to 400 degree Celsius, is applied to the secondary chamber 111 and is monitored by a temperature gauge 110. When optimal values of heat and pressure are achieved inside the secondary chamber 111, the valve 112 is open to release precipitates, obtained by chemical reactions taking place in the secondary chamber 111, into the third chamber 115. The third chamber includes two valves: one for noble gas insertion 113 and the other for plastic fibers or mixture of polymer fibers and extracellular matrix scaffold 114. Optionally, the valve 114 can divide into two to supply the plastic fibers and extracellular matrix scaffold separately. Once the chemical precipitates are deposited on the bottom of the third chamber 115 or top surface of the substrate, preferable calcium carbonate ($CaCO_3$), known as calcite, the pressure cover 118 is closed to apply cold gas isostatic press (room temperature) to the precipitates through the valve 116. The isostatic press process is monitored by a pressure gauge 117.

Figure 2:
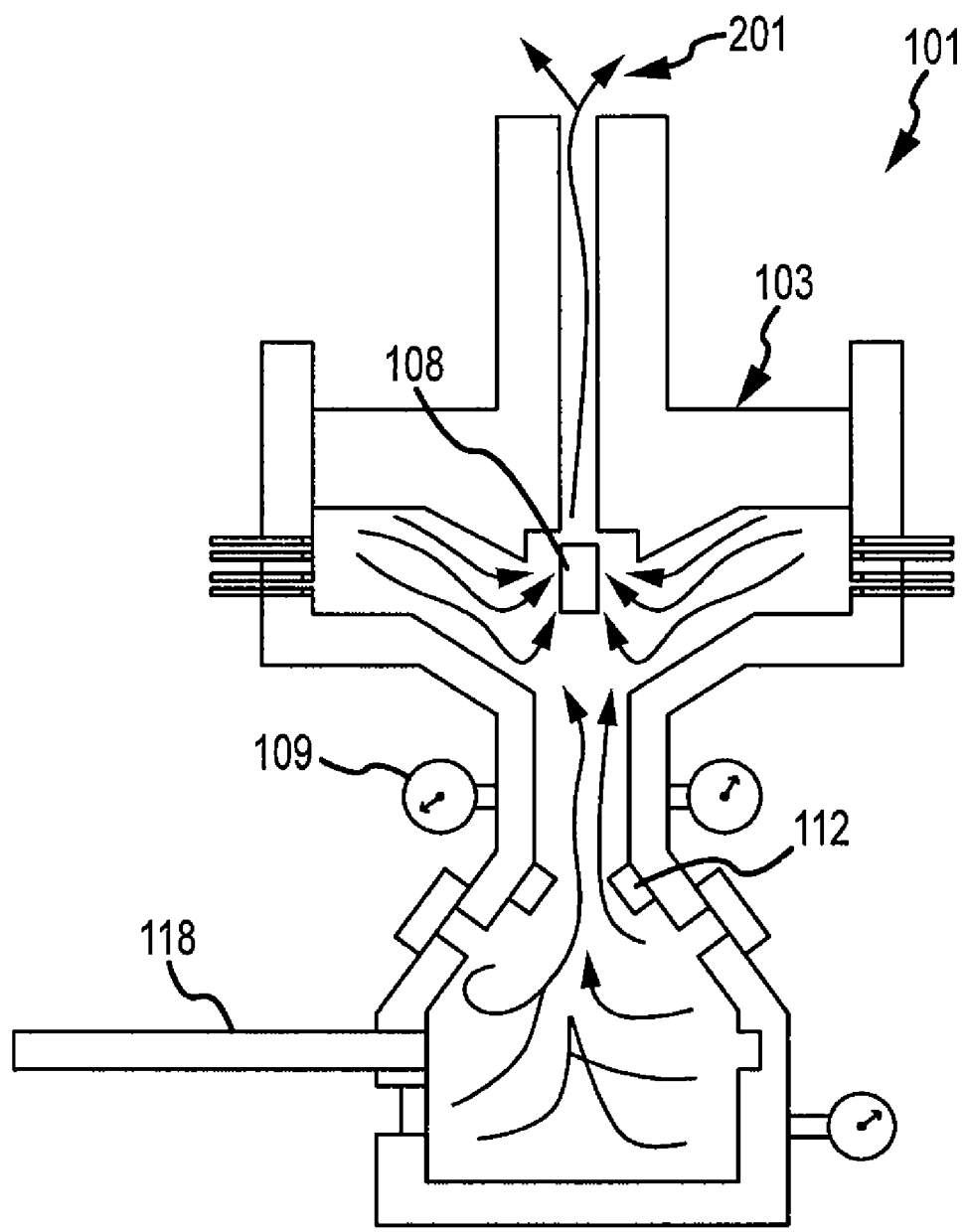
FIG. 2 illustrates an initial vacuum process of the bone substitute material production device of FIG. 1.

To present the production device 101 in further detail, the overall production processes can be divided into five different processes: 1) vacuum process; 2) chemical solution spray process; 3) chemical reaction process; 4) deposition process; and 5) substantially isostatic press process. As shown in FIG. 2, when the piston 103 is at the highest reciprocating position, the valves 108, 112 and pressure cover 118 are open while the other valves are closed. Any gas including air and small residual particles 201 remaining in the chambers is initially removed through the valve 108 using a vacuum device connected to the production device 101. The vacuum process is monitored by a pressure gauge 109 until the chamber achieves at least 70 to 95 percent of vacuum. The additional pressure gauge can be installed onto the device 101 for better monitoring of the vacuum process. Depending on the vacuum state inside the chamber, the optimal amount of the chemical precipitates can be determined.

Figure 3:
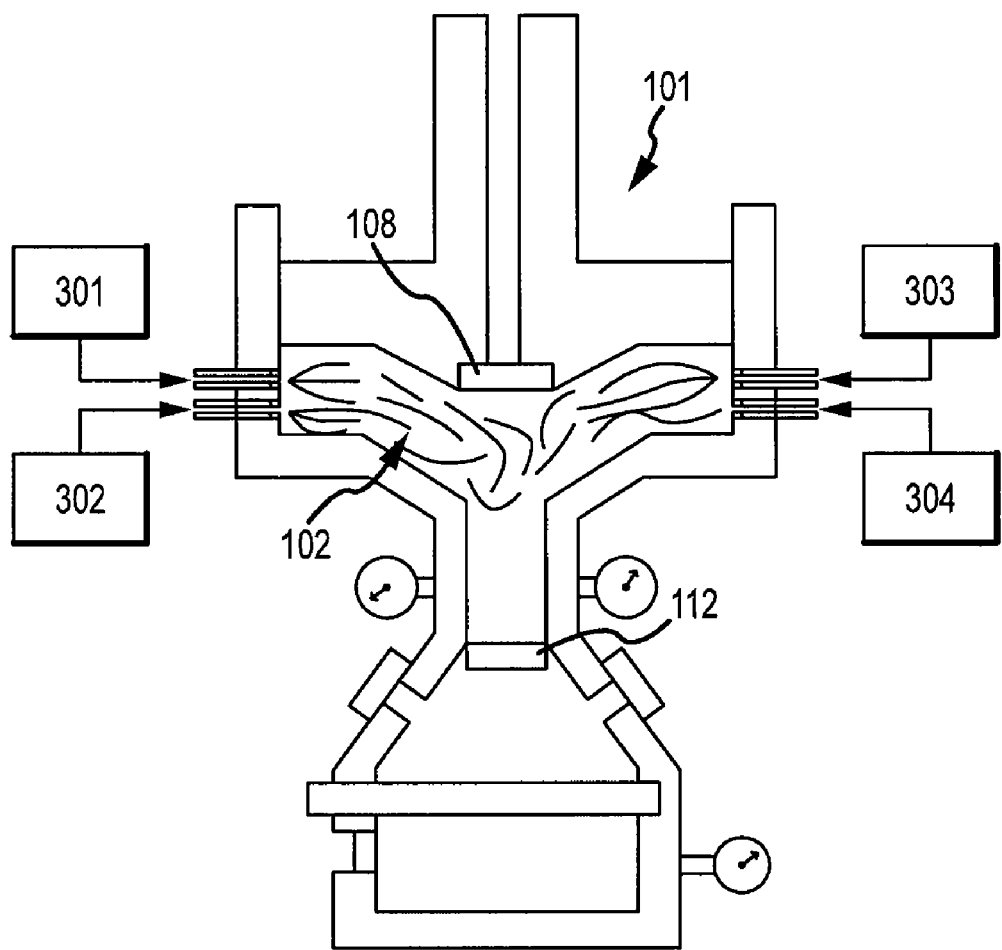
FIG. 3 illustrates a chemical solution spray process of the device of FIG. 1.

As shown in FIG. 3, once the desirable vacuum state is achieved, the chemical solution spray process proceeds. All the valves including 108 and 112 are closed. The containers of 301, 303, 304 and 302 have solutions of $Ca^{++}$ and $Cl^-$, $H(PO_4)^{--}$, $H(CO_3)^-$, and distilled water, respectively. The distilled water is sprayed into the primary chamber to control the solubility of the chemicals during the chemical reactions, i.e. high saturation, low saturation and super saturation. Also, three options are available in this process: (1) all the solutions with $Ca^{++}$ and $Cl^-$, $H(PO_4)^{--}$, $H(CO_3)^-$, are sprayed into the primary chamber 102 to have both calcium phosphate and calcium carbonate minerals; (2) the solutions in containers 301 and 303 are sprayed into the primary chamber 102 to have calcium phosphate mineral only; and (3) the solutions in containers 301 and 304 are sprayed into the primary chamber 102 to have calcium carbonate mineral only. The addition of the calcium carbonate mineral increases the toughness and rigidity of the bone substitute material. Also, the calcium carbonate mineral serves as a growth enhancer to accelerate the formation of the calcium phosphate mineral. However, the calcium carbonate mineral exhibits poor osteoconductive and osteoinductive activities. Therefore, the ratio of calcium phosphate compound to calcium carbonate should be carefully controlled in this process.

Figure 4:
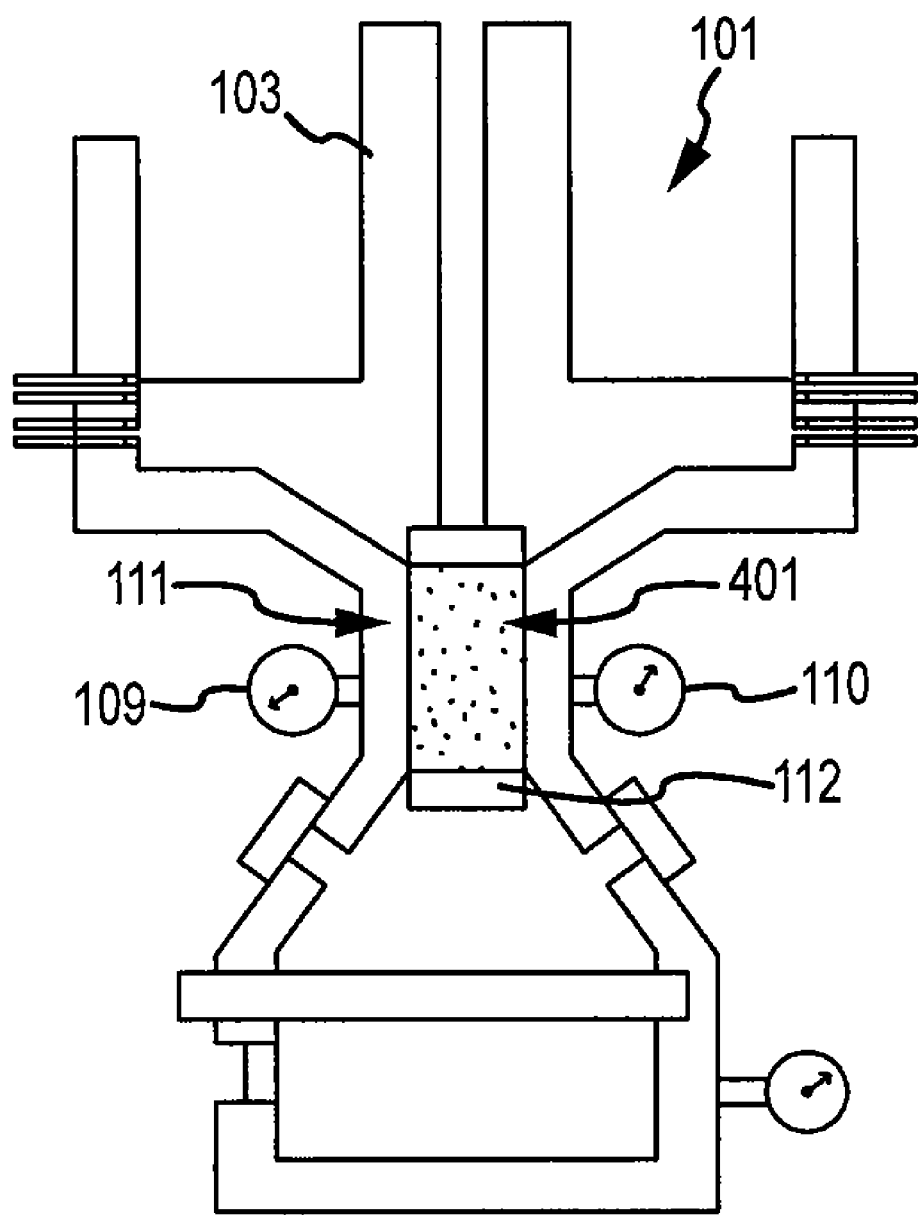
FIG. 4 illustrates an accelerated chemical reaction process of the device of FIG. 1.

As soon as an optimal amount of chemicals is sprayed into the primary chamber 102, the chemical reactions proceed. Each solution particle moves freely inside the primary chamber 102 and collides with other particles. However, in order to accelerate the chemical reaction process and to promote highly homogenous precipitation, the piston 103 moves downward and pushes the chemical solution particles 401 into the secondary chamber 111, as shown in FIG. 4. Because the valve 112 is closed, the downward piston motion creates the pressure inside the secondary chamber 111. Further, heat is applied to the secondary chamber 111, leading to rapid chemical reactions of calcium phosphate and calcium carbonate minerals. The applied heat ranges from room temperature up to 400° C. The controls of pressure and temperature play important roles in chemical reactions of calcium phosphate and calcium carbonate minerals. Optionally, a sensor to monitor pH level can be added in the secondary chamber. Consequently, with a feedback control system, additional calcium, phosphate, carbonate ions and distilled water can be added to adjust pH level. When the calcium chloride solutions reacts with the solution containing dissolved phosphate (e.g., hydrogen phosphate), the phosphate ion is incorporated into the lattice through surface adsorption. The surface density of co-precipitated phosphorus is found to depend on temperature, ionic strength and pH of the solution. Calcium phosphate minerals are not often found in fresh water. The thermodynamically most stable form, at normal temperature and pressure is calcium hydroxyapatite (HAP), but HAP does not form readily in spite of the occurrence of very high supersaturations. Other mineral phases such as DCPD, OCP and amorphous tricalcium phosphate (TCP, β-TCP) form as precursor phases that transform to HAP. Several important factors controlling the precipitation kinetics are: 1) thermodynamic driving force, 2) kinetics of reaction, 3) presence of growth inhibitors, and 4) competing reactions. The presented production device 101 includes the factors 1), 2) and 3). However, competing reactions cannot be incorporated into the device 101 because this requires algae formation or organic matters are involved. Therefore, the production device 101 can systematically provide optimal conditions for chemical reactions with regard to calcium phosphate and calcium carbonate minerals. The optimal conditions of the chemical reactions are monitored by the pressure 109 and temperature 110 gauges with measuring the duration of chemical reaction. In general, when homogenous precipitation occurs, i.e., spontaneous nucleation and growth, unstable amorphous solids or poorly crystalline HAP precede the formation of crystalline HAP. In condition when pH>9, amorphous calcium phosphate mineral is to convert directly into HAP.

Figure 5:
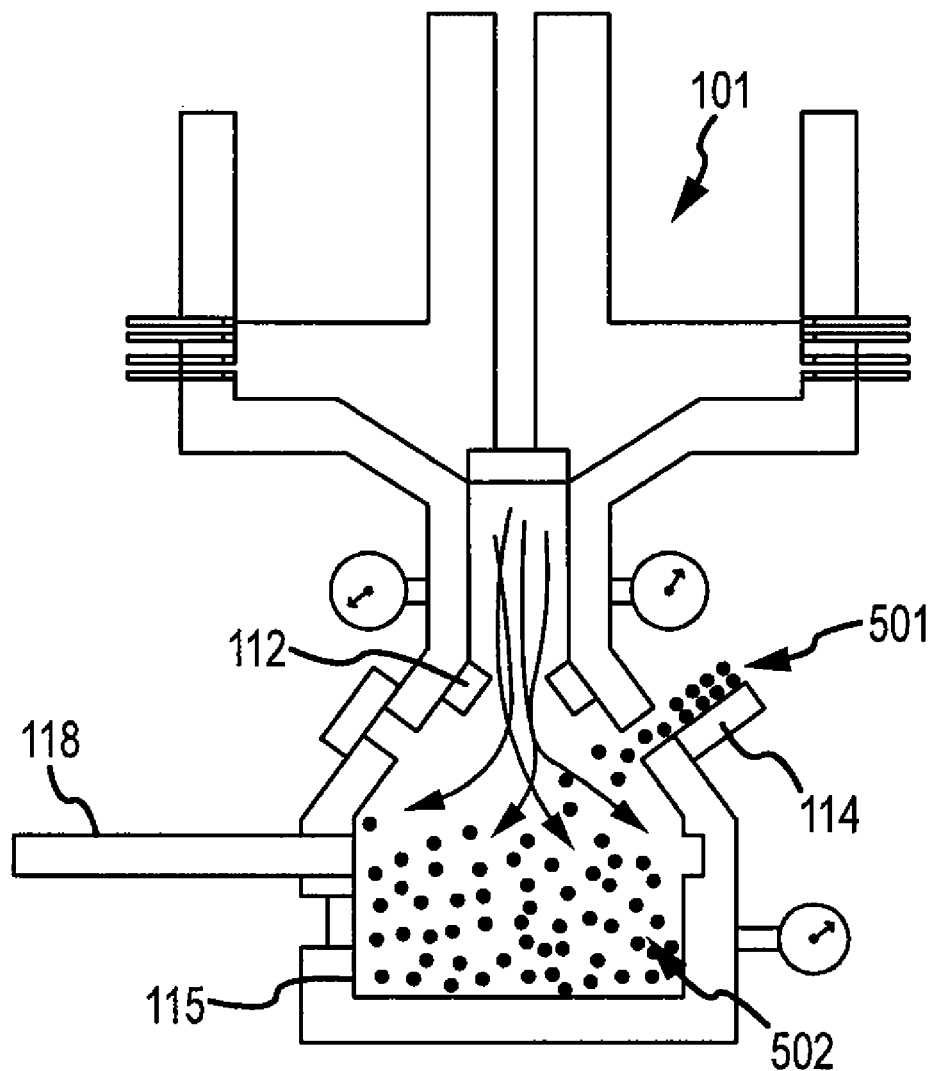
FIG. 5 illustrates a chemical deposition process of the device of FIG. 1.

Once the optimal conditions including the duration of chemical reactions are met, the valve 112 and the pressure cover 118 are open and the precipitates distribute uniformly adjacent to the bottom of the device (top surface of calcium carbonate substrate), shown in FIG. 5. The third chamber 115 is still in a 70-95 percent vacuum state prior to the opening of the valve 112. Further, the valve 114 is open to uniformly distribute biocompatible polymer fibers 501 on the bottom of the third chamber 115, optionally, in combination with extracellular matrix scaffolds (ECM). The volumetric ratio of the polymer fibers 501 to the calcium phosphate mineral 301 should be carefully calculated to obtain the desirable biomechanical properties of the final product according to the laminated theory. The significant process in this stage is the determination of the initial pore size. Pore size strongly depends on the precipitate size of calcium phosphate and calcium carbonate minerals, controlled in the chemical solution spray process of FIG. 3, and volumetric ratio of amount of the precipitates and the third chamber 115. Therefore, the initial pore size can be reasonably controlled with the presented production device 101.

Figure 6:
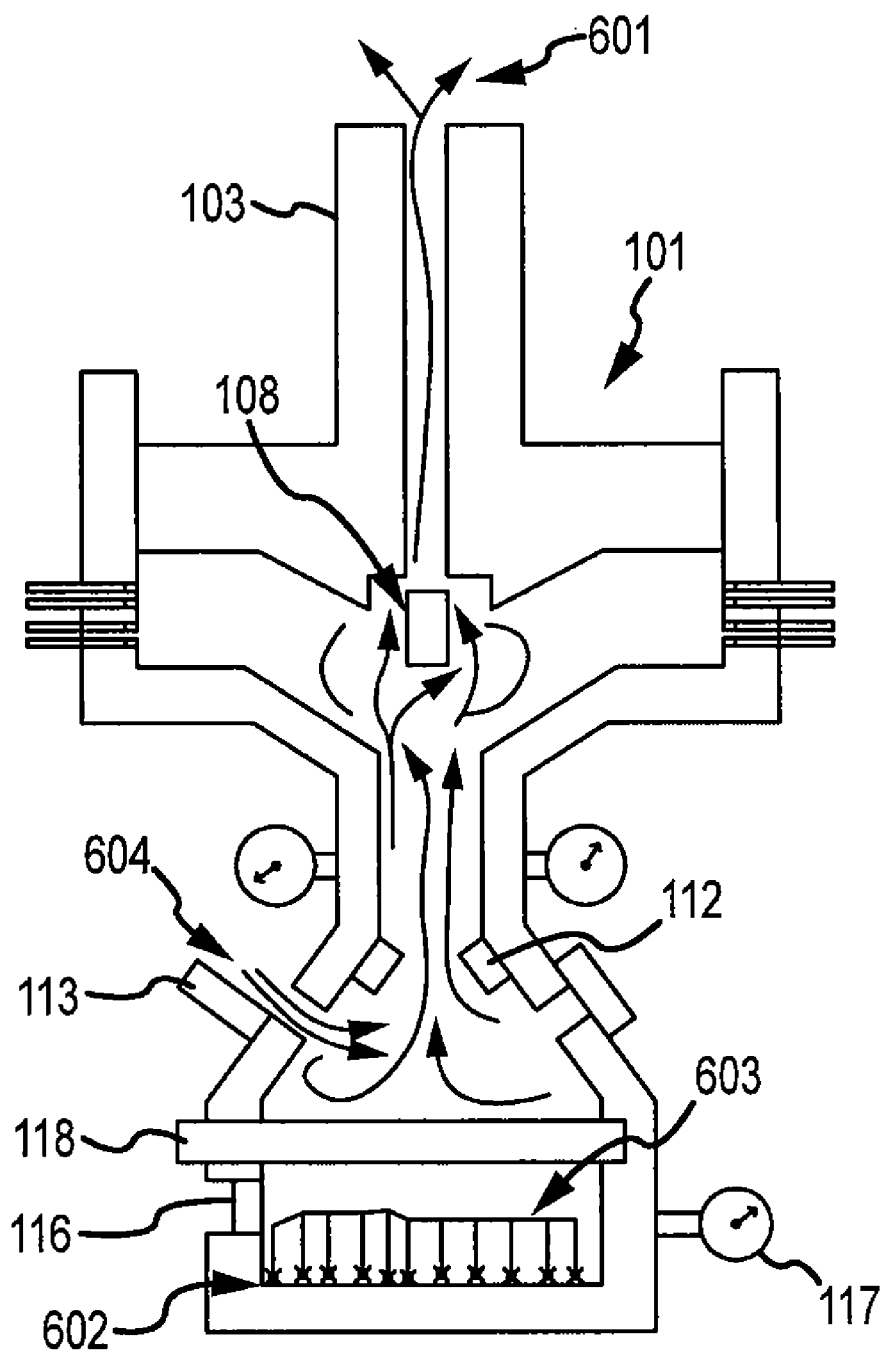
FIG. 6 illustrates isostatic press and noble gas insertion processes of the production device of FIG. 1.

FIG. 6 illustrates the isostatic press process on the precipitates of the production device 101. After the appropriate precipitate thickness of the bone substitute material 602 (e.g., 10-50 μm) is achieved, the pressure cover 118 is closed, and the valve 116 provides high gas pressure 603 to provide the cold gas isostatic press process. At the same time, the valve 113 is open to insert pressurize noble gas 604, such as argon and nitrogen, to remove undesirable chemicals such as hydrochlorine gas HCl(g), residues in solution particles of phosphate and carbonate ions 601, etc. through opened valve 112 and by opening the valve 108 and moving the piston 103 upward. The isostatic press process is monitored by the pressure gauge 117 with the duration of the process.

Figure 7:
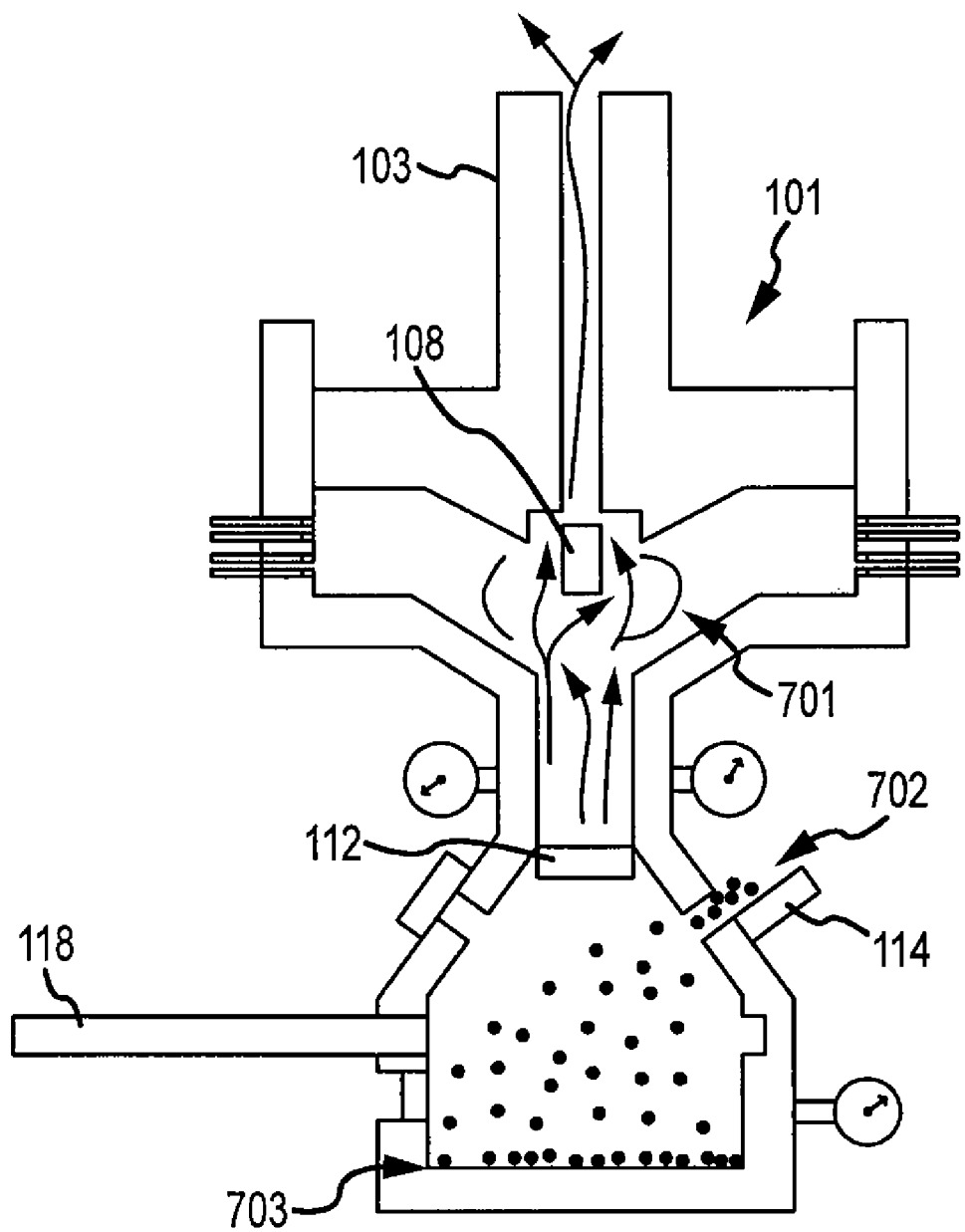
FIG. 7 illustrates a plastic fiber, optionally with extracellular matrix scaffold, deposition process of the device of FIG. 1.

A different approach from that illustrated in FIG. 5 can be made, in which the calcium phosphate minerals and polymer fibers, optionally with ECM, are mixed prior to the isostatic press process in the production device 101. As shown in FIG. 7, the polymer fibers 702 optionally with ECD can be added into the third chamber separately after the isostatic press process. The pressure cover 118 is open, and the valve 112 is closed. It follows that the valve 114 is open to distribute the polymer fibers 702 uniformly on the top surface of the precipitates 703. At the same time, the piston 103 is in the highest position, and the valve 108 is open for all the residual and noble gases 701 to escape from the primary and secondary chambers.

Figure 8:
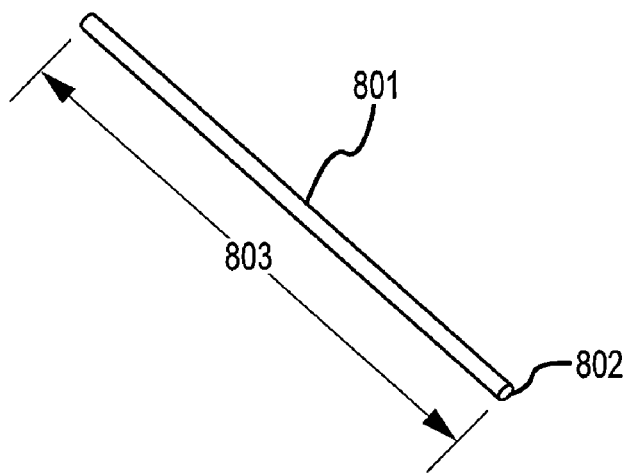
FIG. 8 is a perspective view of a biocompatible polymer fiber.

FIG. 8 shows the perspective view of the biocompatible polymer fiber 801, preferably, PEEK material. The diameter 802 of the polymer fiber 801 ranges from 0.001 to 0.005 inches (0.02 to 0.07 mm), and the ratio of the diameter 802 to length 803 is at least 1 to 10 or higher. The plastic fibers should be uniformly distributed with orthotropic mechanical properties so that the directions of the plastic fibers are only parallel to the bottom surface of the chamber or to the laminar direction.

Figure 9A:
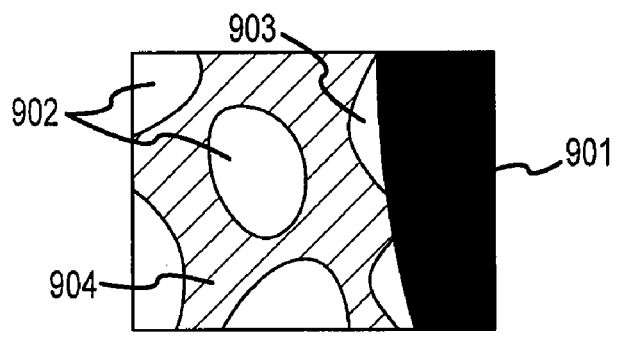
FIGS. 9 a) and b) are respectively microscopic representations before and after the isostatic press process with regard to pore sizes and compactness of a plastic fiber to calcium phosphate deposits of FIG. 6.
Figure 9B:
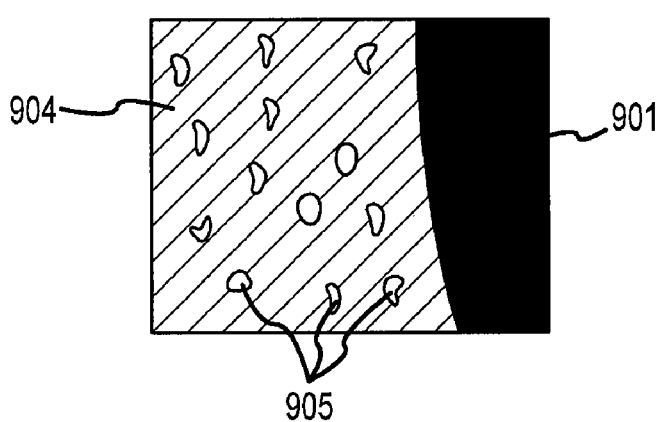

Prior to the isostatic press process, the calcium phosphate minerals in combination with calcium carbonate are accumulated on the bottom of the third chamber. Due to the characteristics of the chemical solution spray deposition shown in FIGS. 3 and 5, the large pore size can be controlled and obtained. FIGS. 9(a) and 9(b) illustrate the porous structures 902 and 905 near the polymer fiber 901 surrounded by the calcium phosphate or calcium carbonate minerals 904 before and after the isostatic press process, respectively. Before the isostatic press process, the pore size is relatively large 902, and the gaps 903 between the calcium phosphate and calcium carbonate minerals 904 and the polymer fiber 901 are formed during the chemical deposition process, shown in FIG. 9 a). However, the isostatic press process provides the reduction of pore size 905 with a significant increase of rigidity and the excellent compactness between the plastic fibers and calcium compounds. During the process, the higher the pressure applies to the third chamber, the higher strength and rigidity the bone substitute material possesses. However, the pressure inside the chamber should be properly controlled to give the good porosity of bone substitute material, leading to an excellent osteoconductive property. It should be noted that too much isostatic press pressure could make the pore size too small or eliminate the porosity.

Figure 10:
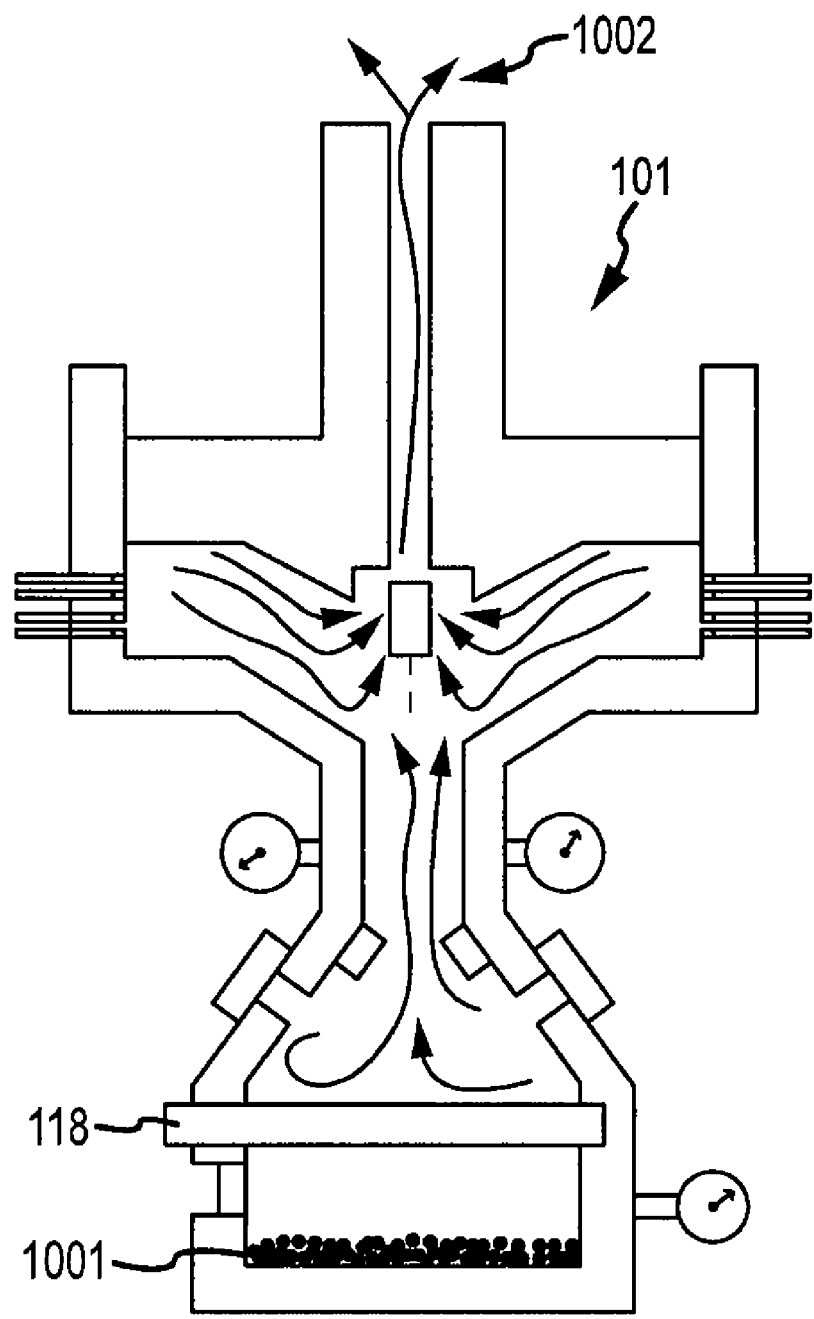
FIG. 10 illustrates a vacuum process of the bone substitute material production device of FIG. 1 after the isostatic press processes of FIG. 6.
Figure 11:
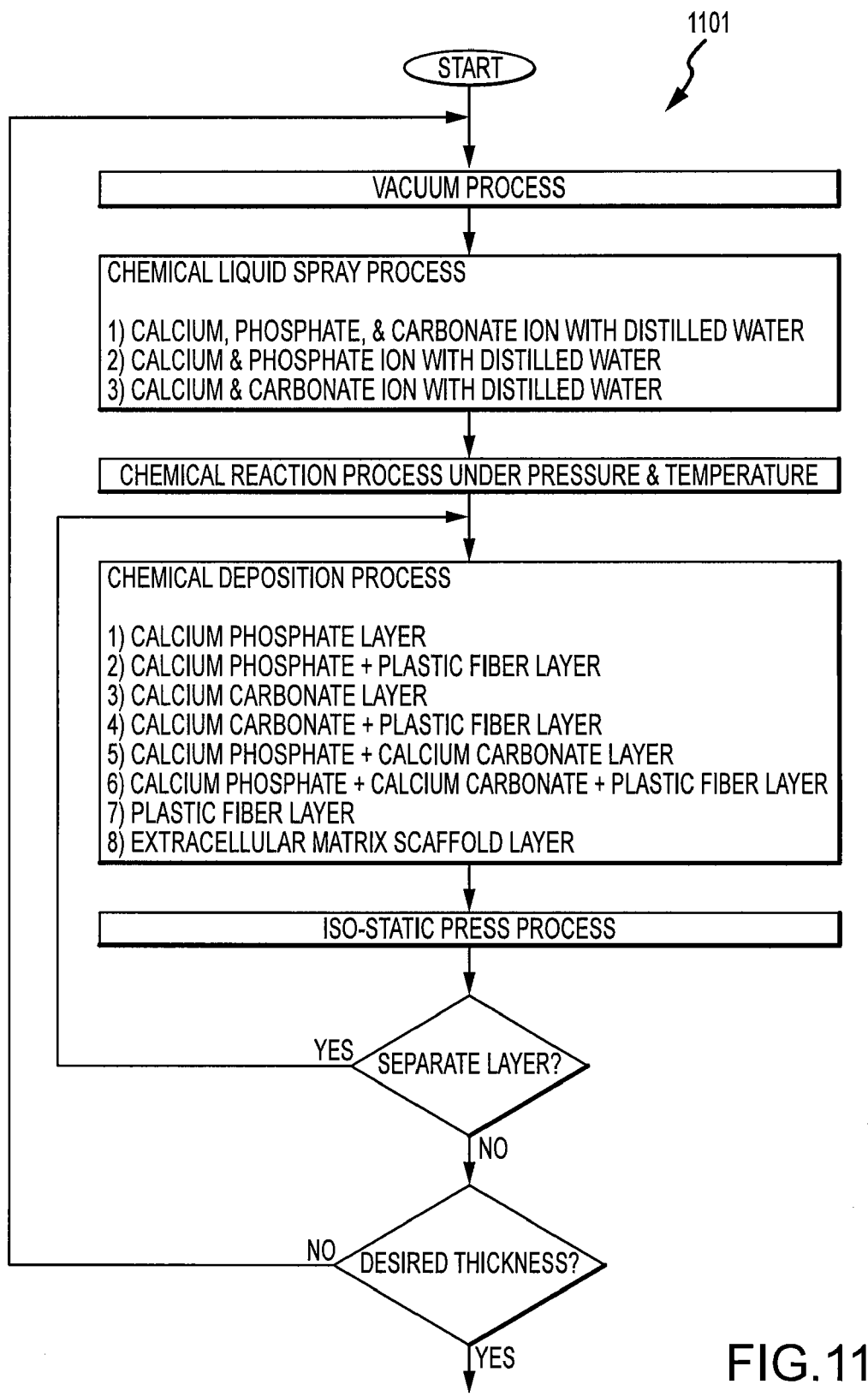
FIG. 11 is a flow chart of the overall production processes of the bone substitute material.

Finally, the vacuum process is repeated as shown in FIG. 10, which illustrates use of a vacuum process in the production device 101 to remove 70 to 95 percent of gases and particles 1002 inside the chambers similar to FIG. 2. However, the difference is that the pressure cover 112 is closed to protect the accumulated bone substitute material 1001 in the third chamber. The processes continuously cycles until the desirable thickness of the bone substitute material is obtained. The flowchart 1101 of the overall processes of the production device is shown in FIG. 11, which illustrates the five different stages of production of the bone substitute material with several options as described above. Once the bulk of the bone substitute material is obtained from the production device 101, it is transferred to another isostatic press chamber, and optionally, an additional isostatic press process can be performed applying hydrostatic pressure using saline solution, which can be also used for cleaning and chemical disinfection.

Figure 12:
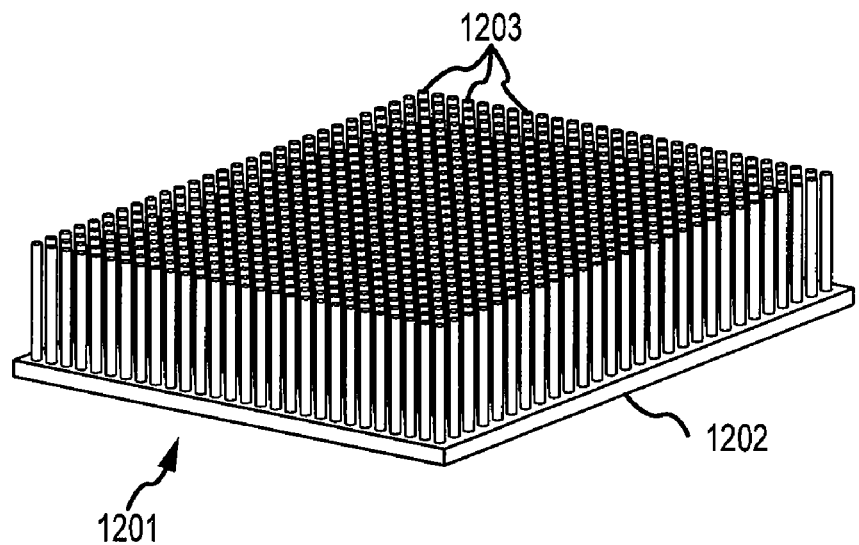
FIG. 12 illustrates a perspective view of a through-hole mechanical device to simulate blood canals of natural bone.
Figure 13:
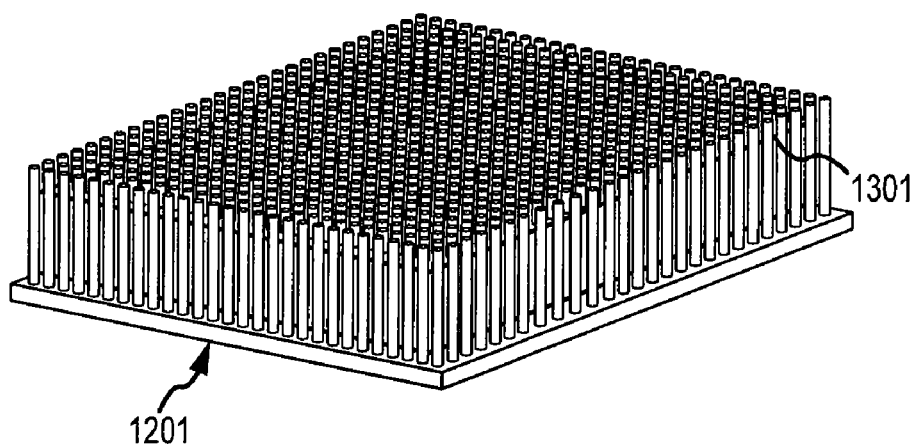
FIG. 13 illustrates a perspective view of the through-hole mechanical device of FIG. 11 with accumulated calcium based bone substitute.
Figure 14:
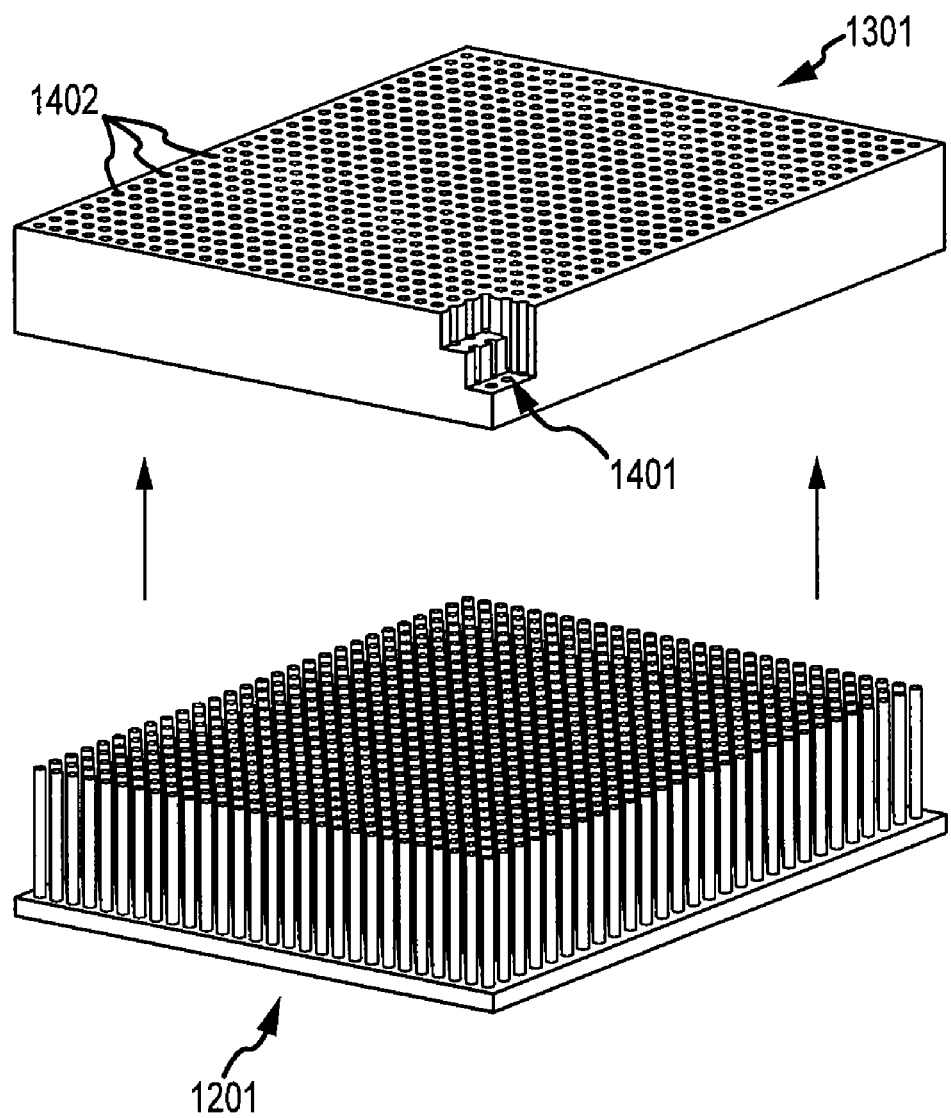
FIG. 14 illustrates a perspective view of the accumulated calcium based bone substitute separated from the through-hole device of FIG. 11.
Figure 15:
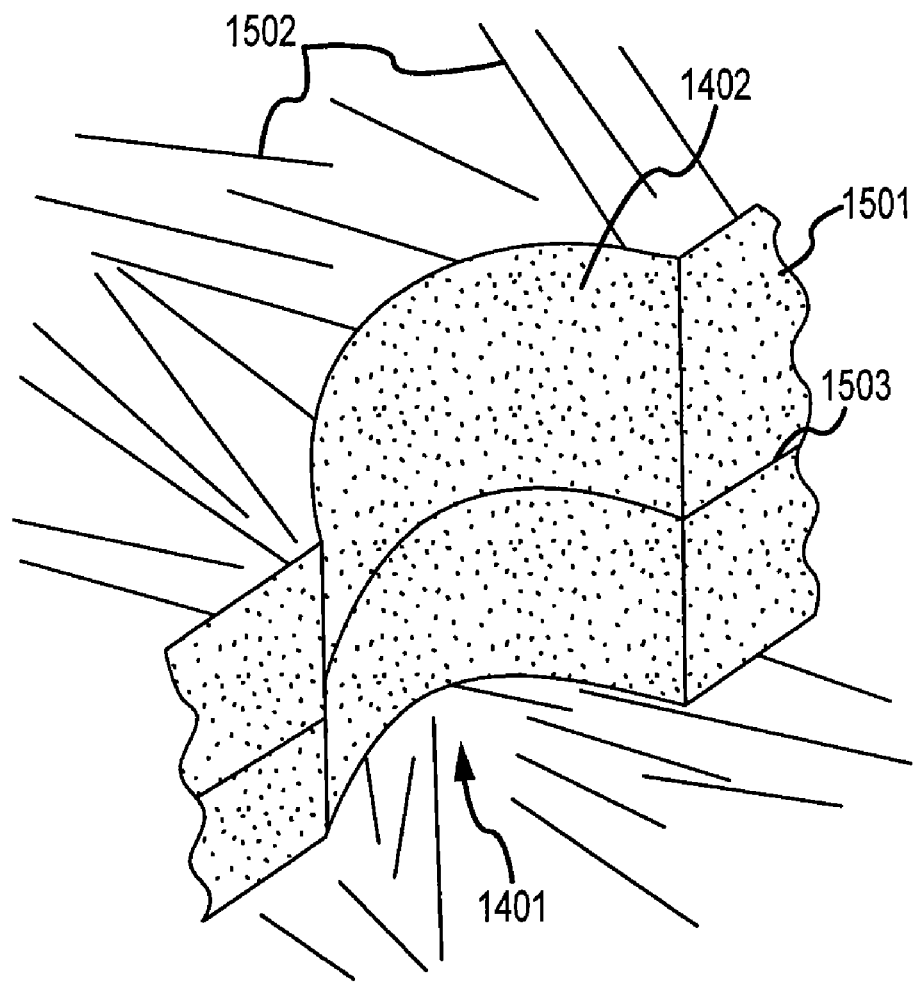
FIG. 15 is a magnified view of section 1301 of FIG. 13.

FIG. 12 illustrates the mechanical through-hole device 1201 to create macro size apertures of diameter 0.2-4 millimeters (preferably, 0.5-2 mm) in the bone substitute material. The device 1201 consists of a stainless steel plate 1202 and numerous hardened stainless steel rods 1203 with dimensions of 0.5 to 2 mm in diameter and 30 to 40 mm in length. The steel rods 1203 are uniformly distributed and attached (welded or brazed) onto the plate 1202. The mechanical through-hole device 1201 is placed on the bottom of the third chamber in the production device 101. FIG. 13 illustrates the bone substitute material 1301 accumulated on the mechanical through-hole device 1201. After the desired thickness is obtained, the bone substitute material 1301 and device 1201 are taken out from the production device 101. It follows that the bone substitute 1301 is separated from the device 1201. As shown in FIG. 14, the bone substitute material block 1301 contains many uniformly distributed through holes 1402. The through holes 1402 play a very important role in osteoinduction prior to surgeries. In combination with bone morphogenetic protein (BMP), the through holes increase the osteoinductive activities when bone substitute is inserted into the body. FIG. 15 is a magnified view of section 1401 around the through-hole 1402 in FIG. 14. The line 1503 represents the borderline resulting from the repeated isostatic pressed laminated layers 1501 of the bone substitute mineral. The polymer fibers 1502 are uniformly distributed parallel to the laminar direction with the random orientation on the laminate layer 1501 to provide the orthotropic mechanical property.

Figure 16:
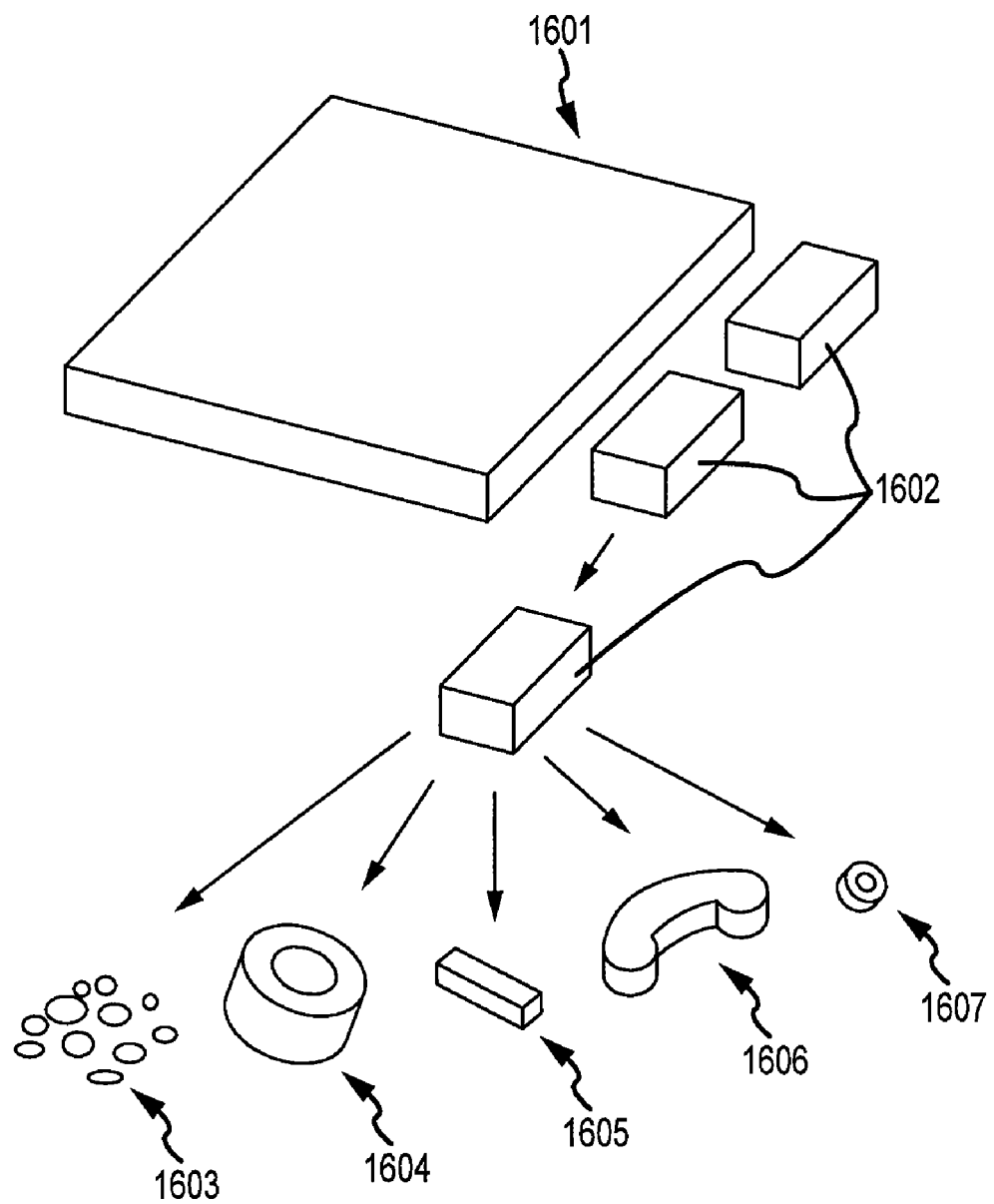
FIG. 16 illustrates fabrication of the bone substitute material for applications in orthopedic areas including load bearing spinal fusion.

As shown in FIG. 16, the bulk of bone substitute material 1601 can be used in many different applications including load bearing in the orthopedic industry. The bone substitute can be crushed by a bone grinder to produce the bone substitute powder 1603 with the size of around 50 to 200 micrometers for general bone healing surgeries. Furthermore, the sliced piece 1602 of the bone substitute material 1601 can be fabricated for many different types of spinal implants. Spine inter-body fusion is performed from cervical, posterior, anterior or transversely oriented positions. Cervical and posterior lumbar inter-body fusion (PLIF) involve making an incision along a center line on the posterior side of the neck and lower back, respectively. Cervical 1607 and posterior lumbar 1605 inter-body implants can be made from the piece 1602 of the bone substitute material. Furthermore, transforaminal lumbar inter-body fusion (TLIF) is an improvement of the PLIF procedure in which the spine is approached transversely or posterolaterally, from a side of a patient. ALIF refers to anterior lumbar inter-body fusion. This procedure is similar to TLIF, but is performed from the front (anterior) of the body, usually through a minimal incision in the lower left lower abdominal area. The ALIF 1604 and TLIF 1606 implants are also shown in FIG. 16. Success or failure of the surgery depends in part on whether the insert stably remains at the location, and on whether the implant induces new bone formation. The presented bone substitute material undergoes the production processes to provide the characteristics to be an excellent osteoconductive biocompatible material such as biochemical compatibility and biomechanical comparability, especially load bearing applications. In combination with BMP and ECM, the excellent osteoinduction can occur to promote new bone formation. In load bearing applications, spinal inter-body fusion between two adjacent bodies is recognized and encouraged for good biomechanical, neurophysiological and anatomical practices.

Figure 17:
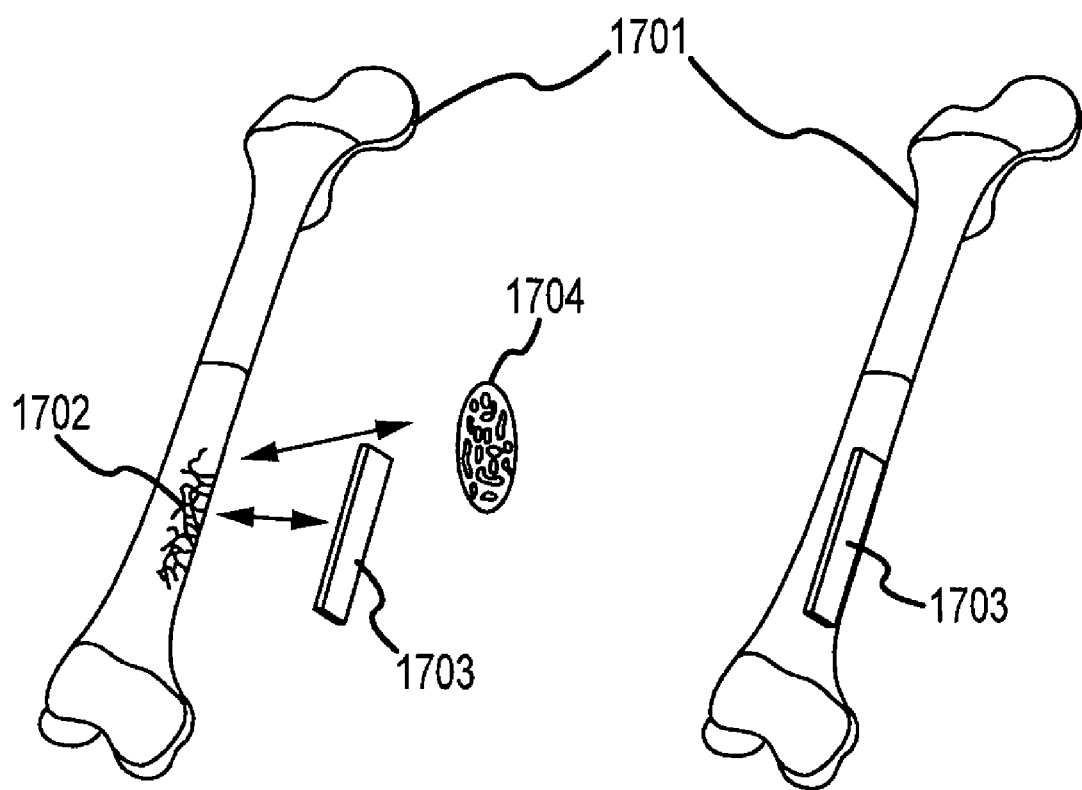
FIG. 17 illustrates another application of the bone substitute material in a long bone fracture.

FIG. 17 illustrates a human femur 1701 having multiple cracks and fractures 1702. Based upon the results of computer tomography (CT) and/or magnetic resonance imaging (MRI) scan images, especially the surface area adjacent to the damaged region 1702 of the femur 1701, the bone substitute material 1703 is fabricated with a thickness in a range 3-5 mm to match and provide good contact with the damaged bone surface region. The bone substitute material 1703 is tightly fixed onto the damaged surface region using bone screws and/or other biocompatible screws. The bone substitute material 1703 can provide a significant increase in osteogenesis in the damaged bone surface region, as well as temporary protection of the damaged bone over a reasonable time interval. Alternatively, osteogenesis activity can be promoted by wrapping the ground bone 1603 of FIG. 16 with a biocompatible membrane 1704 and attaching the membrane to the damaged region, in combination with the BMP. FIG. 17 illustrates application of the bone substitute material to a long bone structure.

What is claimed is:

1. A bone substitute material comprising:
   a substrate;
   at least one layer comprising calcium phosphate minerals disposed on the substrate;
   at least one layer comprising calcium carbonate minerals disposed on the at least one layer of calcium phosphate, and
   biocompatible polymer fibers deposited with the at least one layer of calcium phosphate or the at least one layer of calcium carbonate,
   wherein the layers are individually formed during an isostatic press process, and
   wherein the bone substitute material has a ratio of calcium to phosphate of approximately 1.6 and has at least 70 MPa of compressive strength.

2. The bone substitute material of claim 1 wherein the biocompatible polymer fibers are polyetheretherketone (PEEK) fibers.

3. The bone substitute material of claim 1 further comprising extracellular matrix scaffold proteins.

4. The bone substitute material of claim 3 wherein the extracellular matrix scaffold proteins are selected from the group consisting of collagen, laminin, fibronectin and glycosaminoglycans.

5. An orthopedic implant comprising the bone substitute material of claim 1.

6. The bone substitute material of claim 1 further comprising uniformly distributed through holes configured to promote osteoinduction.

7. A bone substitute material comprising:
   a substrate;
   at least one layer comprising calcium phosphate and calcium carbonate minerals disposed on the substrate, and
   biocompatible polymer fibers deposited in a random orientation relative to the at least one layer of calcium phosphate and calcium carbonate minerals,
   wherein the at least one layer is formed during an isostatic press process, and
   wherein the bone substitute material has a ratio of calcium to phosphate of approximately 1.6 and has at least 70 MPa of compressive strength,
   wherein the biocompatible polymer fibers are polyetheretherketone (PEEK) fibers.

8. The bone substitute material of claim 7 further comprising extracellular matrix scaffold proteins.

9. The bone substitute material of claim 8 wherein the extracellular matrix scaffold proteins are selected from the group consisting of collagen, laminin, fibronectin and glycosaminoglycans.

10. An orthopedic implant comprising the bone substitute material of claim 7.

11. The bone substitute material of claim 7 further comprising uniformly distributed through holes configured to promote osteoinduction.

* * * * *